Patent Number: 4,870,098
… Date of Patent: Sep. 26, 1989

[54] ANTAGONISTS OF LEUKOTRIENE D₄

[75] Inventors: Michael A. Stealey, Libertyville; Richard M. Weier, Lake Bluff, both of Ill.

[73] Assignee: G. D. Searle & Co., Chicago, Ill.

[21] Appl. No.: 298,156

[22] Filed: Jan. 17, 1989

[51] Int. Cl.⁴ ............... C07D 327/04; C07D 339/06; A61K 31/385; A61K 31/39
[52] U.S. Cl. ........................... 514/439; 514/440; 514/462; 549/30; 549/39; 549/40; 549/342
[58] Field of Search ........ 549/454, 30, 40, 39, 549/342; 514/462, 439, 440

[56] References Cited

U.S. PATENT DOCUMENTS 4,710,505 12/1987 Robin et al. .................. 514/278
4,808,729 2/1989 Deason et al. ................. 549/30

FOREIGN PATENT DOCUMENTS 1448340 7/1965 France .
1445013 7/1966 France .

OTHER PUBLICATIONS

McCarthy, et al., J. Med. Chem., 28: 1145–1147 (1985).
Derwent World Patent Index, 88-030227/05.

*Primary Examiner*—Richard A. Schwartz
*Assistant Examiner*—E. B. Magrab
*Attorney, Agent, or Firm*—Paul D. Matukaitis; Joy Ann Serauskas

[57] ABSTRACT

This invention encompasses compounds of Formula I

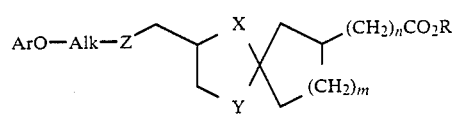

and the pharmaceutically acceptable salts and geometrical and optical isomers thereof wherein:
  Alk is alkylene or hydroxyalkylene containing 1-6 carbon atoms;
  Ar is 5,6,7,8-tetrahydro-1-naphthalenyl or phenyl optionally substituted with one or more substituents selected from lower alkyl containing 1 to 6 carbon atoms, hydroxy, lower alkoxy containing 1 to 6 carbon atoms, or lower alkanoyl containing 1 to 6 carbon atoms;
  R is hydrogen and lower alkyl containing 1 to 6 carbon atoms;
  X, Y, and Z are each independently O or S with S optionally oxidized to S=O;
  m is an integer from 0 to 3;
  n is an integer from 0 to 5.

The compounds are useful as anti-allergy agents and anti-inflammatory agents.

13 Claims, No Drawings

ANTAGONISTS OF LEUKOTRIENE D4

BACKGROUND OF THE INVENTION

1. Field of the Invention

This invention is in the field of pharmaceutical agents which act as leukotriene D4 (LTD4) antagonists and includes embodiments which act as leukotriene B4 (LTB4) antagonists.

2. Prior Art

The prior art generally describes LTD4 antagonists as anti-allergy compounds and LTB4 antagonists as anti-inflammatory agents.

Leukotriene D4 and C4 (LTD4/LTC4) and leukotriene B4 (LTB4) are products of the archidonic acid metabolic pathway. LTD4 and LTC4 are associated with smooth muscle contraction and contract guinea pig ileum, human and guinea pig bronchi and human pulmonary artery and vein. LTB4 is associated with neutrophil stimulation and is characterized by chemotaxis, aggregation and degranulation. LTB4 is believed to be an important mediator of inflammation. High levels of LTB4 are detected in rheumatoid arthritis, gout, psoriasis, and inflammatory bowel disease. Thus antagonists of LTB4 are useful in the therapy of such diseases.

Dioxolane-2-carboxylic acids of the formula

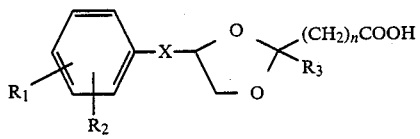

where $R_1$ and $R_2$ are the same or different H, halogen, alkyl, or alkoxy;
$R_3$ is H, alkyl, aryl or alkyl optionally substituted by halogen, lower alkyl, or lower alkoxy;
X is —CH$_2$—, —OCH$_2$— where the O is joined to the phenyl;
n is 0–3,
are taught as sedatives or choleretic agents in French Pat. No. 1,445,013.

SUMMARY OF THE INVENTION

This invention encompasses novel compounds of the hereinafter described Formula I, pharmaceutical formulations containing such compounds, and the use of these formulations as anti-allergy agents and anti-inflammatory agents.

DETAILED DESCRIPTION

This invention encompasses compounds of Formula I

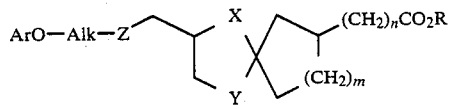

and the pharmaceutically acceptable salts and geometrical and optical isomers thereof wherein:
Alk is alkylene or hydroxyalkylene containing 1-6 carbon atoms;
Ar is 5,6,7,8-tetrahydro-1-naphthalenyl, or phenyl optionally substituted with one or more substituents selected from lower alkyl containing 1 to 6 carbon atoms, hydroxy, lower alkoxy containing 1 to 6 carbon atoms, and lower alkanoyl containing 1 to 6 carbon atoms;
R is hydrogen or lower alkyl containing 1 to 6 carbon atoms;
X, Y, and Z are each independently O or S with S optionally oxidized to S=O;
m is an integer from 0 to 3;
n is an integer from 0 to 5.

A preferred embodiment of the present invention is a compound of the formula

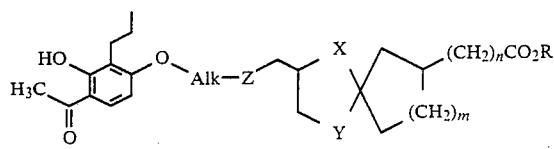

and the pharmaceutically acceptable salts and geometrical and optical isomers thereof wherein:
Alk is alkylene or hydroxyalkylene containing 1-6 carbon atoms;
R is hydrogen or lower alkyl containing 1 to 6 carbon atoms;
X, Y and Z are each independently O or S with S optionally oxidized to S=O;
m is an integer from 0 to 3;
n is an integer from 0 to 5.

The term "lower alkyl" means straight or branched chain alkyl having 1 to 6 carbon atoms such as methyl, ethyl, propyl, butyl, pentyl, hexyl and the branched chain isomers thereof.

The term "lower alkoxy" means straight or branched chain alkoxy having 1 to 6 carbon atoms such as methoxy, ethoxy, propoxy, butoxy, pentoxy, hexoxy and the branched chain isomers thereof.

The term "lower alkanoyl" means straight or branched chain alkanoyl having 2 to 6 carbon atoms such as acetyl, propanoyl, butanoyl, pentanoyl, hexanoyl and the branched chain isomers thereof.

The term "alkylene" means straight or branched chain alkylenes having 1 to 6 carbon atoms such as methylene, ethylene, trimethylene, methylethylene and tetramethylene.

The term "pharmaceutically acceptable salts" means non-toxic salts of the acids of the compounds of this invention where the cation is sodium, potassium, lithium, calcium, magnesium, zinc, ferrous, aluminum, ammonium, tetraalkylammonium, and the like.

Compounds of this invention are generally prepared according to the following schemes:

SCHEME A

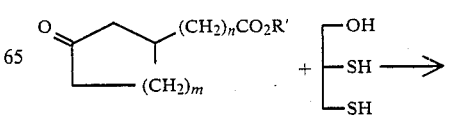

3
-continued
SCHEME A
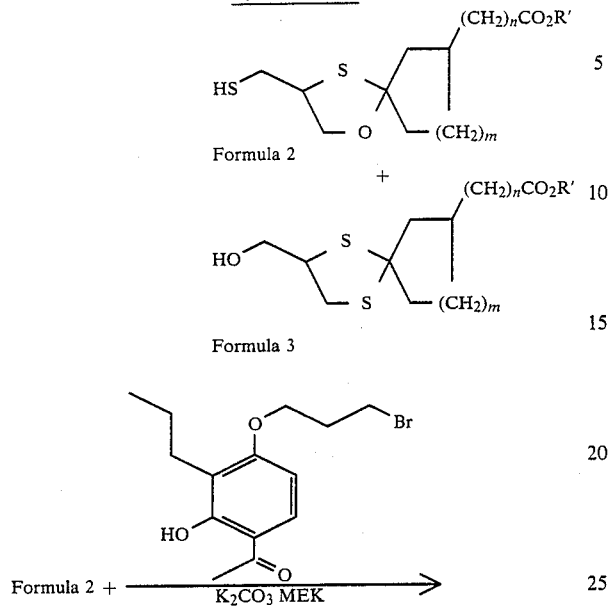
Formula 2
Formula 3
Formula 2 + [aryl bromide] $\xrightarrow{K_2CO_3 \text{ MEK}}$
4
-continued
SCHEME A
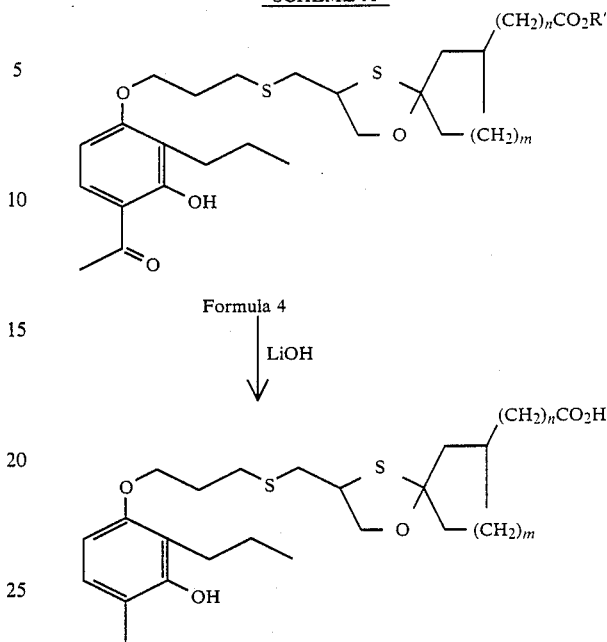
Formula 4
↓ LiOH
Formula 5
m is an integer from 0 to 3
n is an integer from 0 to 5
R' is an alkyl containing 1 to 6 carbon atoms
SCHEME B
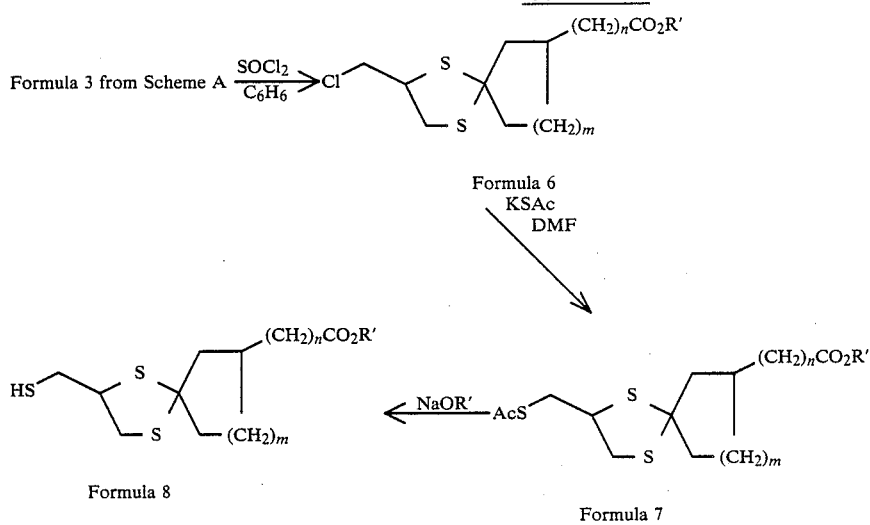
Formula 3 from Scheme A $\xrightarrow{SOCl_2}{C_6H_6}$
Formula 6
KSAc
DMF
Formula 8 ← $\xleftarrow{NaOR'}$ AcS— Formula 7
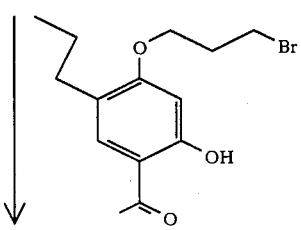
$K_2CO_3$ -continued
SCHEME B
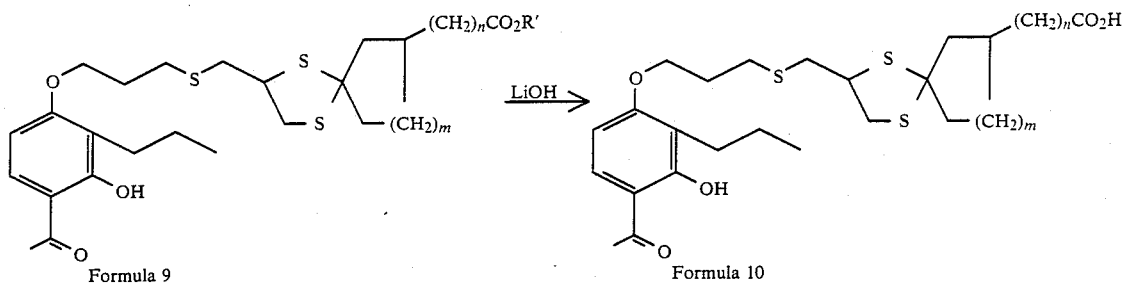
Formula 9 → Formula 10
m is an integer from 0 to 3
n is an integer from 0 to 5
R' is an alkyl containing 1 to 6 carbon atoms
SCHEME C
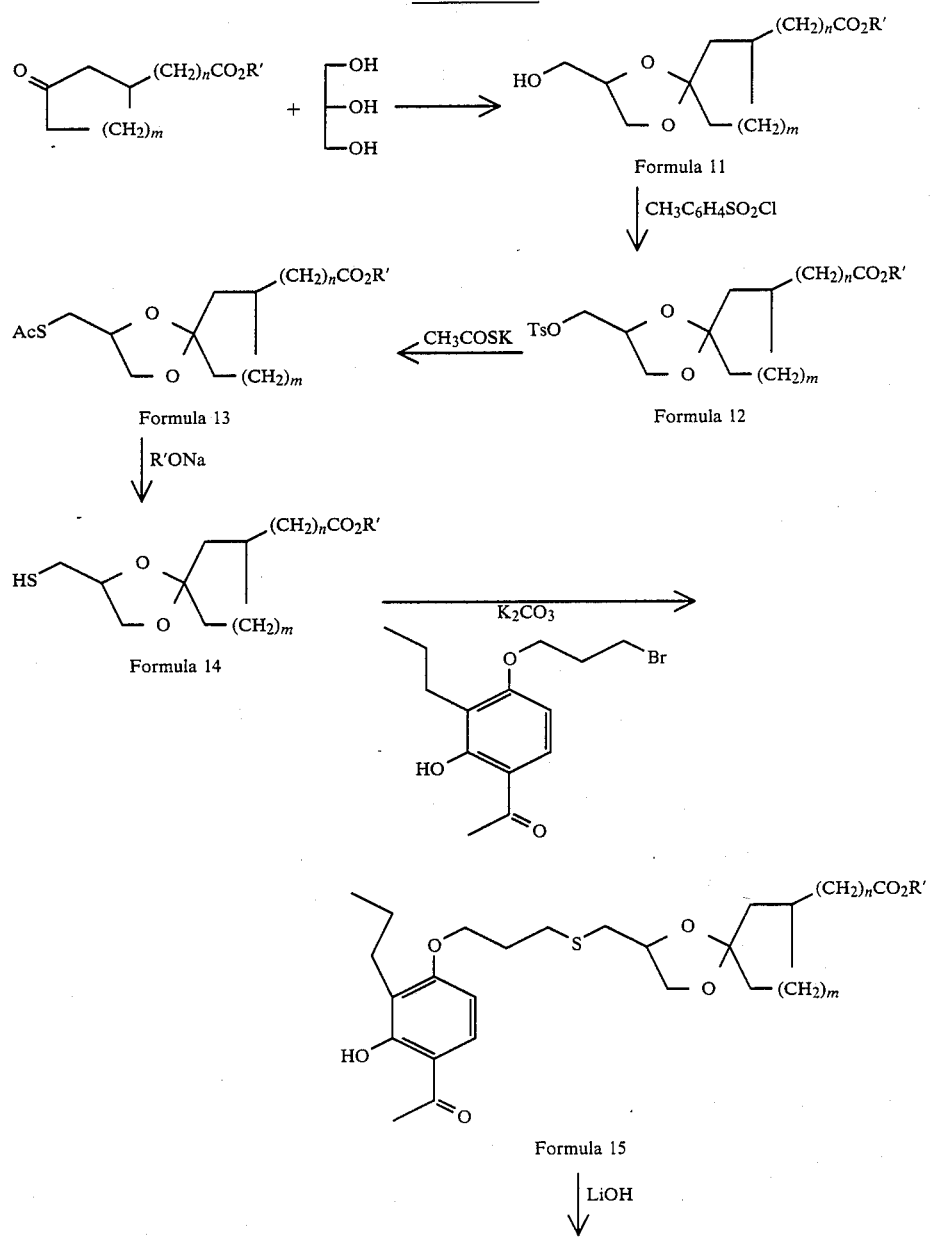

-continued
SCHEME C
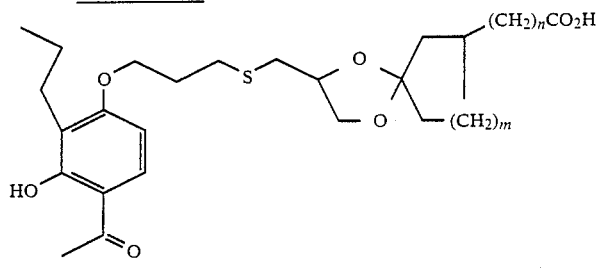
Formula 16
m is an integer from 0 to 3
n is an integer from 0 to 5
R' is an alkyl containing 1 to 6 carbon atoms
SCHEME D
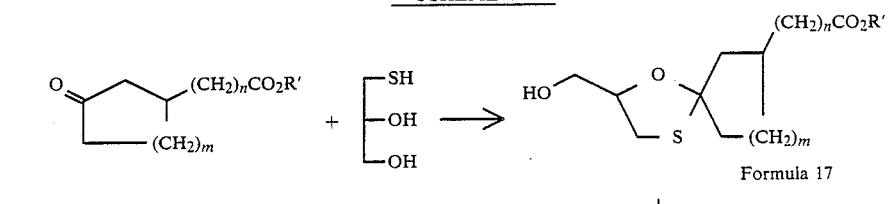
Formula 17
↓ CH₃C₆H₄SO₂Cl
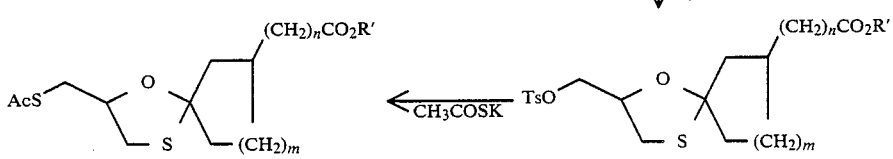
Formula 19 ← CH₃COSK  Formula 18
↓ R'ONa
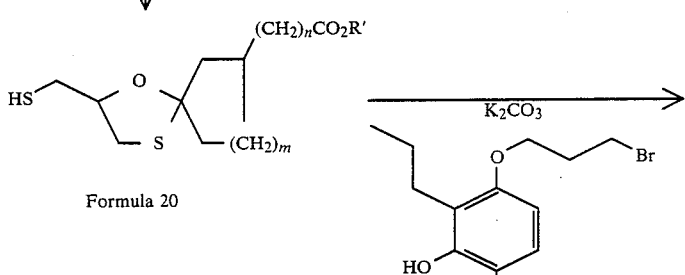
Formula 20
K₂CO₃ →
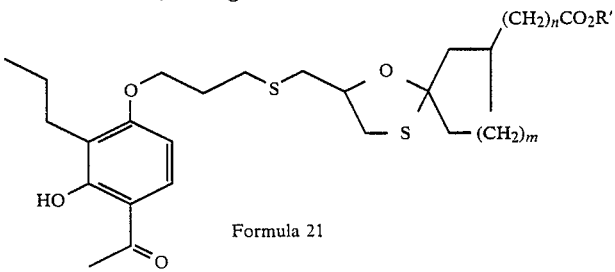
Formula 21
↓ LiOH

-continued
SCHEME D

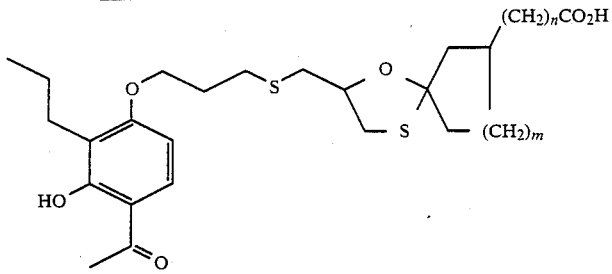

Formula 22 m is an integer from 0 to 3
n is an integer from 0 to 5
R' is an alkyl containing 1 to 6 carbon atoms

Scheme A

The compounds of Formula I wherein X and S, Y is O and Z is S and remaining definitions are as defined before are prepared according to Scheme A. An appropriate ketoester which is prepared according to the procedure described in Bartlett and Woods, *J. Am. Chem. Soc.*, 62, 2933 (1949) is reacted with 2,3-dimercapto-1-propanol in the presence of an organic solvent such as benzene and a mineral acid such as hydrochloric acid. The reaction results in the products which are represented by Formula 2 and Formula 3.

The products which are represented by Formula 2 are further treated with 3-(2-n-propyl-3-hydroxy-4-acetyl phenoxy)-1-bromo propane which is described in U.S. Pat. No. 4,565,882 in the presence of an organic solvent such as methyl ethyl ketone and potassium carbonate to give the compounds of Formula 4=the compounds wherein the R of Formula I is alkyl containing 1 to 6 carbon atoms=with the proviso that these compounds could be further treated with lithium hydroxide to give compounds of Formula I wherein R is hydrogen. It is understood that the compounds which are represented by Formula 4 and Formula 5 are racemic mixtures.

Scheme B

The compounds of Formula I wherein X, Y, Z are all S and the remaining definitions are as defined before are prepared according to Scheme B. The compounds which are represented by Formula 3 are treated with thionyl chloride in an organic solvent such as benzene to give the compounds of Formula 6. These compounds are further treated with a mixture of potassium thioacetate in N,N,-dimethylformamide to give the compounds of Formula 7. Conversion of the thioacetate compounds of Formula 7 to the mercaptan compounds of Formula 8 is accomplished by treating the thioacetate compounds with the appropriate sodium alkoxide. Treatment of the mercaptan compounds of Formula 8 with 3-(2-n-propyl-3-hydroxy-4-acetyl phenoxy)-1-bromo propane and potassium carbonate results in the compounds of Formula 9. Treatment of compounds of Formula 9 with lithium hydroxide gives the compounds of Formula 10. It is understood that the compounds represented by Formula 9 and Formula 10 are mixtures of racemates.

Scheme C

The compounds of Formula I wherein X is O, Y is O and Z is S and the remaining definitions are as defined before are prepared according to Scheme C. A ketoester which is prepared according to the procedure described in Bartlett and Woods, *J. Am. Chem. Soc.*, 62, 2933 (1940) is reacted with glycerol in the presence of an organic solvent such as benzene and p-toluenesulfonic acid to give the compound represented by Formula 11. The compounds represented by Formula 11 are treated with p-toluenesulfonyl chloride in the presence of pyridine to give the compounds represented by Formula 12. The compounds of Formula 12 are reacted with potassium thioacetate in the presence of acetone to give the compounds of Formula 13. Compounds of Formula 13 are treated with the appropriate sodium alkoxide to give the compounds of Formula 14. Compounds of Formula 14 are reacted with 3-(2-n-propyl-3-hydroxy-4-acetylphenoxy)-1-bromopropane which has been prepared according to the procedure described in U.S. Pat. No. 4,565,882 in the presence methyl ethyl ketone to give the compounds of Formula 15. When the compounds of Formula I wherein R is hydrogen are desired, compounds of Formula 15 can be treated with lithium hydroxide to give the compounds represented by Formula 16. It is understood that the compounds which are represented by Formulas 15 and 16 are racemic mixtures.

Scheme D

The compounds of Formula I wherein X is O, Y is S and Z is S and the remaining definitions are as defined before are prepared according to Scheme D. A ketoester which is prepared according to the procedure described in Bartlett and Woods, *J. Am. Chem. Soc.*, 62, 2933 (1940) is reacted with 3-mercapto-1,2 propanediol in the presence of a mineral acid or Lewis acid such as BF$_3$ etherate in methylene chloride to give the compound represented by Formula 17. The compounds represented by Formula 17 are treated with p-toluenesulfonyl chloride in the presence of pyridine to give the compounds represented by Formula 18. The compounds of Formula 18 are reacted with potassium thioacetate in the presence of acetone to give the compounds of Formula 19. Compounds of Formula 19 are treated with the appropriate sodium alkoxide to give the compounds of Formula 20. Compounds of Formula 10 are reacted with 3-(2-n-propyl-3-hydroxy-4acetylphenoxy-1-bromopropane which is prepared according to the procedure described in U.S. Pat. No. 4,565,882 in the presence of methyl ethyl ketone to give the compounds of Formula 21. When the compounds of Formula I wherein R is hydrogen are desired compounds of Formula 21 can be treated with lithium hydroxide to give the compounds represented by Formula 22. It is understood that the compounds which are represented by Formulae 21 and 22 are racemic mixtures.

In all schemes 3-(2-n-propyl-3-hydroxy-4-acetyl-phenoxy)-1-bromopropane was exemplified in that phase of the reaction sequence in which the side chain (left hand side portion of the molecule represented by Formula I) introduction was taught. It is understood that replacement of the bromide compound with a 5,6,7,8-tetrahydro-1-naphthalenyloxy or a phenoxyalkyl bromide compound and following the reaction sequences which are described in Schemes A, B, C and D will result in the compounds of Formula I wherein Ar is 5,6,7,8-tetrahydro-1-naphthalenyl or phenyl and the remaining definitions are as described.

Optical isomers are resolved into enantiomers by conventional techniques.

The $LTD_4$ antagonist utility compounds are illustrated by activity in one or more of the following tests.

$LTD_4$ Antagonism in Guinea Pig Ileum

Fresh segments of guinea pig ileum were suspended in 2 ml. tissue baths containing oxygenated modified Tyrodes solution. After an equilibration period, an agonist dose-response curve was generated by exposing each tissue to 4 different $LTD_4$ doses and measuring the ensuing contractile heights. The ileum segments were washed and rested between exposures to agonist. Following this, the tissues were incubated with a single concentration of test compound and the agonist dose-response procedure was repeated. The dose ratio is a measure of the antagonist's ability to shift the agonist dose-response curve to the right. It is derived as the concentration of agonist necessary to reach a given response level in the presence (A') versus the absence (A) of antagonist. For example, if the test concentration of compound had no effect on the agonist-induced response (A'=A) the dose-ratio would approximate 1. Dose-ratios increase if the compound inhibits the agonist-induced response. One dose-ratio value is determined for each strip of ileum used to test antagonist. If the dose-ratios increase as a function of increasing antagonist concentration, these data may be evaluated by Schild analysis to determine whether the inhibition is competitive and if so, what the $pA_2$ value is for that compound. Schild analysis examines the linearity of the function described by the dose-ratios written as log [(A'/A)-1] versus antagonist concentration. If the linearity is confined and the slope approximates 1, inhibition is considered to be competitive. The $pA_2$ is the negative log of the antagonist concentration required to produce a dose-ratio of 2. This value is considered to be a measure of the affinity of the competitive antagonist.

In Vivo Assay

The compounds are tested in vivo as follows. Adult male fasted Hartly guinea pigs weighing 300–350 g are pretreated with pyrilamine and indomethacin to block the bronchoconstricture effects of endogenous histamine and the synthesis of thromboxane $A_2$ respectively. Compounds of the invention are administered IV or IG at appropriate times prior to the IV administration of 2000 units of $LTD_4$. Intratracheal pressure is monitored prior to and subsequent to $LTD_4$ in animals anesthetized with pentobarbital and attached to a rodent respirator. Compounds which antagonize the direct component of $LTD_4$ action on respiratory smooth muscle inhibit intratracheal insufflation pressure increases ($P <$ or $=0.05$) caused by $LTD_4$. FPL 55712 is used as a control.

Leukotriene Receptor Binding Assay

The in vitro $LTD_4$ receptor binding assay is carried out as follows:

Specific binding of titrated $LTD_4$ to a fixed number of guinea pig lung receptors, isolated from guinea pig lung membrane, is measured in the presence and absence of test compound. The initial screening dose ($1 \times 10^{-5}$M) is considered active if the specific binding of the $LTD_4$ is reduced by 45% or more. Active compounds are tested in a dose-response manner to determine $IC_{50}$ values.

$LTB_4$ activity of compounds of this invention is indicated by the following tests.

Preparation of Human Neutrophils

Neutrophils are purified from venous blood of normal human donors using standard techniques of dextran sedimentation, centrifugation on Histopaque sterile solution (Sigma) and hypotonic lysis of erythrocytes (Boyum, A., *Isolation of Leukocytes From Human Blood: Further Observations*. Scand. J. Lab. Clin. Invest. 21 (Suppl. 97): 31, 1968). The purity of isolated neutrophils was $\geq 95\%$.

$LTB_4$ Receptor Binding Assay

Neutrophils ($4-6 \times 10^6$) in 1 ml Hanks' balanced salt solution containing 10 mM HEPES buffer (HBSS), pH 7.4 and 30 mM nordihydroguaiaretic acid were incubated with 0.6 nano M ($^3$H) $LTB_4$ in the presence or absence of test compounds. The incubation was carried out at 0° C. for 45 minutes and terminated by adding 5 ml of ice-cold HBSS followed by rapid filtration of incubation mixture under vacuum through GF/C glass fiber filters. The filters were further washed with 10 ml HBSS and radioactivity was determined. Specific binding was defined as the difference between total binding and nonspecific binding which was not displayed by $10^{-7}$M unlabeled $LTB_4$. All data refer to specific binding.

Human Neutrophil Degranulation Assay

Neutrophil degranulation was determined by measuring the release of myeloperoxidase activity into the incubation medium. Neutrophils ($3 \times 10^6$) in 1 ml HBSS solution were preincubated with cytochalasin B(5$\mu$g) at 37° C. for 5 minutes, followed by preincubation with test compounds for 7 minutes. Neutrophils were then incubated for 2 to 20 minutes with either $LTB_4$ ($5 \times 10^{-8}$M) or the chemotactic peptide f-met-leu-phe ($5 \times 10^{-6}$M) to induce degranulation. Following incubation, samples were centrifuged and myeloperoxidase was extracted from the cell pellets by sonication in phosphate buffer containing 0.4% Triton X-100. Triton X-100 was also added to the supernatants to a concentration of 0.4%. The supernatants and the pellet-extracts were then assayed spectrophotometrically for myeloperoxidase activity by determining the rate of decomposition of $H_2O_2$ with o-dianisidine as hydrogen donor as described by Renlund, et al. (Renlund, D. G., MacFarlane, J. L., Christensen, R. D., Lynch, R. E., and Rothstein, G., *A Quantitive And Sensitive Method for Measurement of Myeloperoxidase*, Clinical Research 28:75A, 1980). Myeloperoxidase activity released into the supernatant was expressed as the percent of the average total activity (pellet plus supernatant).

Guinea Pig LTB$_4$-Induced Dermal Chemotaxis

Test compound was administered intravenously or intragastrically at various times prior to the injection of leukotriene B$_4$ (LTB$_4$). LTB$_4$ was diluted in phosphate buffered saline (PBS) and 35 ng in 0.2 ml were injected intradermally into the shaven backs of anesthetized guinea pigs. PBS was injected as control. Four hours later, animals were sacrificed, skins removed and stored frozen ($-70°$ C.). Injection sites were removed with a skin punch and mechanically homogenized (Polytron, Brinkmann Instruments). Myeloperoxidase (MPO), a marker enzyme for neutrophils, was extracted by 0.5% hexadecyltrimethylammonium bromide in 50 mM potassium phosphate buffer (pH 6.0), using sonication and freeze-thaw procedures. After centrifugation ($40,000 \times g$, 30 minutes), enzyme activities in the supernatants were assayed spectrophotometrically ($A_{460}$) by measuring the decomposition of hydrogen peroxide with ortho-dianisidine after 15 minutes. MPO activity was found to be proportional to the number of neutrophils. In guinea pigs the level of MPO activity increased with the amount of LTB$_4$ injected.

Modified Boyden Chamber Chemotaxis

Human neutrophils were isolated from citrated peripheral blood sedimented in 5% dextran, followed by centrifugation on Histopaque sterile solution (Sigma) and hypotonic lysis of erythrocytes. A final cell suspension of $3-4 \times 10^6$ neutrophils/ml of HEPES-buffered Hanks' balanced salt solution (HBSS, pH 7.3) was added to the upper well (0.8 ml) of a modified Boyden chamber (blind well). The lower well (0.2 ml), separated by a polycarbonate membrane (Nuleopore Corp.), contained HBSS or $3 \times 10^{-8}$M LTB$_4$ in the presence or absence of test compound. Following a 90 minute incubation at 37°C. in 5% CO$_2$-95% air, cells from the lower well were lysed and nuclei counted in a Model S-Plus-IV Coulter counter. Percent inhibition was calculated from cell counts corrected from random migration by subtracting the mean of the HBSS control.

Table I illustrates the LTD$_4$ and LTB$_4$ activity of a representative compound of the present invention.

TABLE I

| | LTD$_4$ ANTAGONISM | | |
|---|---|---|---|
| Example | Receptor Binding Assay (IC$_{50}$) | Guinea Pig Ileum Assay (pA$_2$) | In Vivo Bronchoconstriction Assay (% Inhibition at 5 mpk. IV) |
| 2 | 6.15 μM | 7.34 | 94.7 |

| | LTB$_4$ ANTAGONISM | | |
|---|---|---|---|
| Example | Receptor Binding Assay (IC$_{50}$) | Human Neutrophil Degranulation (IC$_{50}$) | Guinea Pig LTB$_4$ Induced Dermal Chemotaxis (IC$_{50}$) |
| 2 | 0.8 μM | 7.3 μM | 8.3 μM |

The compounds can be administered in such oral dosage forms as tablets, capsules, softgels, pills, powders, granules, elixirs, or syrups. The compounds can also be administered intravascularly, intraperitoneally, subcutaneously, or intramuscularly, using forms known to the pharmaceutical art. In general, the preferred form of administration is oral. For the orally administered pharmaceutical compositions and methods of the present invention the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, softgels, elixirs, syrups, drops, and the like, and consistent with conventional pharmaceutical practices.

For example, for oral administration in the form of tablets or capsules, the active drug components can be combined with any oral non-toxic pharmaceutically acceptable inert carrier such as lactose, starch, sucrose, cellulose, magnesium stearate, dicalcium phosphate, calcium sulfate mannitol, and the like, or various combinations thereof. For oral administration in liquid forms, such as in softgels, elixirs, syrups, drops and the like, the active drug components can be combined with any oral non-toxic pharmaceutically acceptable inert carrier such as water, saline, ethanol, polyethylene glycol, propylene glycol, corn oil, cottonseed oil, peanut oil, sesame oil, benzyl alcohol, various buffers, and the like, or various combinations thereof. Moreover, when desired or necessary suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes, or combinations thereof. Lubricants for use in these dosage forms include boric acid, sodium benzoate, sodium acetate, sodium chloride, and the like, or combinations thereof. Disintegrators include, without limitation, starch, methyl-cellulose, agar, bentonite, guar gum, and the like, or combinations thereof. Sweetening and flavoring agents and preservatives can also be included where appropriate.

For intravascular, intraperitoneal, subcutaneous, or intramuscular administration, active drug components can be combined with a suitable carrier such as water, saline, aqueous dextrose, and the like. Regardless of the route of administration selected, the compounds of the present invention are formulated into pharmaceutically acceptable dosage forms by conventional methods known to those skilled in the art. The compounds can also be formulated using pharmacologically acceptable base addition salts. Moreover, the compounds or their salts can be used in a suitable hydrated form.

Topical formulations of salves and ointments are useful in treating conditions such as psoriasis.

Regardless of the route of administration selected, a non-toxic but therapeutically effective quantity of one or more compounds of this invention is employed in any treatment. The dosage regimen for preventing or treating inflammatory conditions with the compounds of this invention is selected in accordance with a variety of factors, including the type, age, weight, sex, and medical condition of the patient, the severity of the inflammatory condition, the route of administration, and the particular compound employed in the treatment. A physician or veterinarian of ordinary skill can readily determine and prescribe the effective amount of the drug required to prevent or arrest the progress of the condition. In so proceeding, the physician or veterinarian could employ relatively low doses at first and subsequently increase the dose until a maximum response is obtained. Daily dosages of the compounds of the invention are ordinarily in the range of about 1 to 50 mg/kg are generally suitable.

The accompanying examples illustrate the methods used to prepare the compounds of this invention. These examples are given by way of illustration only and in no way should be construed as limiting the invention in spirit or in scope, as many modifications in materials and methods will be apparent from this disclosure to those skilled in the art.

Preparation of Starting Material

Example A

Preparation of ethyl 3-(mercaptomethyl)-1-oxa-4thiaspiro[4.4]nonane-7-acetate

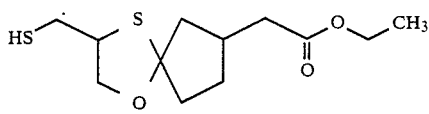

To a stirred solution of ketoester (9.23 g, 0.054 moles) and 2,3-dimercapto-1-propanol (7 g, 0.054 moles) in benzene (75 ml) was added concentrated hydrochloric acid (10 drops). After 3 days at room temperature under a nitrogen atmosphere, the reaction mixture was poured into 5% aqueous $K_2CO_3$ (100 ml) and extracted with ethyl ether. The organic layer was washed with saturated sodium chloride solution and dried over sodium sulfate. The drying agent was filtered and the filtrate concentrated on the rotary evaporator to give a crude oil (14 g). Chromatography of the crude product on silica gel using 15% ethyl acetate/hexane as the eluent gave 2.1 g of the titled compound as a mixture of four racemates in a ratio of 1.0:1.25:1.25:1.3 as determined by $^{13}$C nmr.

Anal. Calcd. for $C_{12}H_{20}S_2O_3$: C, 52.16; H, 7.29; S, 23.16. Found: C, 52.31; H, 7.45; S, 23.43.

Example B

Preparation of ethyl 2-(hydroxymetnyl)-1,4-dithiaspiro[4.4]nonane-7-acetate

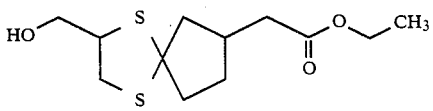

Continued chromatography using the same solvent system as described in Example A of ethyl 3-(mercaptomethyl)-1-oxa-4-thiaspiro[4.4]nonane-7-acetate gave 6.5 g of the titled compound as a mixture of racemates.

Example C

Preparation of ethyl 3-(mercaptomethyl)-1-oxa-4-thiaspiro[4.5]decane-7-acetate

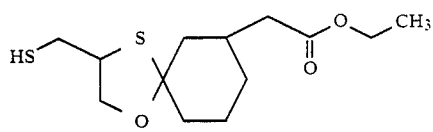

The titled compound was prepared from the appropriate ketoester (7.3 g, 0.04 mol) and 2,3-dimercapto-1-propanol (5.0 g, 0.04 mol) using the procedure described in Example A. Chromatography of the crude product on silica gel using 30% ethyl acetate/hexane as the eluent gave the titled compound as a mixture of four racemates.

Example D

Preparation of ethyl 2-(hydroxymethyl)-1,4-dithiaspiro[4.5]decane-7-acetate

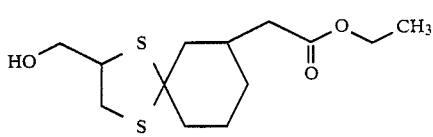

The titled compound was prepared using the crude product of Example C and the procedure of Example B.

Anal. Calcd. for $C_{13}H_{22}S_2O_3$: C, 53.78; H, 7.63; S, 22.05. Found: C, 53.50; H, 7.86; S, 22.40.

Example E

Preparation of ethyl 2-(chloromethyl)-1,4-dithiaspiro[4.4]nonane-7-acetate

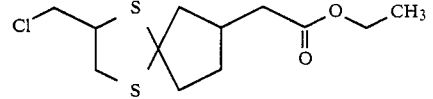

A solution of product of Example B (4.4 g, 0.016 moles) and thionyl chloride (2.3 g, 0.019 moles) in benzene (30 ml) was refluxed under nitrogen for 1 hr. The reaction was cooled and washed with 4% sodium bicarbonate solution and saturated brine and dried ($Na_2SO_4$). The drying agent was filtered and the filtrate stripped on the rotary evaporator to give an oily residue. The crude product was chromatographed on silica gel using 5% ethyl acetate/hexane to give 4 g of the titled compounds.

Anal. Calcd. for $C_{12}H_{19}ClS_2O_2$: C, 48.90; H, 6.49; S, 21.71. Found: C, 48.65; H, 6.67; S, 21.45.

Example F

Preparation of ethyl 2-[(acetylthio)methyl]-1,4-dithiaspiro[4.4]nonane-7-acetate

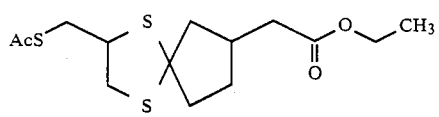

A mixture of potassium thioacetate (5.4 g, 0.047 mole) and a solution of the product of Example E (4.0 g, 0.013 mole) in DMF (40 ml) was stirred under nitrogen for 2 days at room temperature. The reaction mixture was diluted with water (200 ml) and extracted twice with ethyl acetate. The organic phase was washed with brine and dried ($Na_2SO_4$). The drying agent was filtered and the filtrate stripped on the rotary evaporator to give 4.5 g of the titled compound. This material was a single spot on TLC.

Example G

Preparation of ethyl 2-(mercaptomethyl)-1,4-dithiaspiro[4.4]nonane-7-acetate

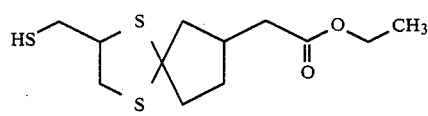

A solution of the product of Example F and sodium ethoxide (prepared from 350 mg of sodium metal) in absolute ethanol (40 ml) was stirred for 1 hr under nitrogen. The reaction mixture was poured into 200 ml of 0.5N $KHSO_4$ and extracted with ethyl acetate. After drying the organic phase over sodium sulfate, the solvent was removed on the rotary evaporator and the residue was chromatographed on silica gel using 5% ethyl acetate/hexane to give 2.1 g of the titled compound.

Anal. Calcd. for $C_{12}H_{20}S_3O_2$: C, 49.31; H, 6.89; S, 32.84. Found: C, 49.45; H, 6.95; S, 32.67.

Example H

Preparation of ethyl 2-(chloromethyl)-1,4-dithiaspiro[4.5]decane-7-acetate

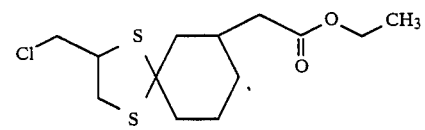

The titled compound was prepared according to the procedure described in Example E using 6.2 g (0.021 mole) of the product of Example D and 2.75 g (0.025 mol) of thionyl chloride in benzene (60 ml). The crude product was chromatographed on silica gel using 5% ethyl acetate/hexane to give two sets of two racemates. The less polar pair of racemates weighed 0.62 g. The more polar pair of racemates weighed 1.3 g.

Example I

Preparation of ethyl 2-[(acetylthio)methyl]-1,4-dithiaspiro[4.5]decane-7-acetate

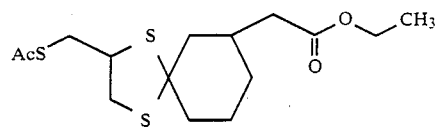

The titled compound was synthesized according to the procedure used for the synthesis of the thioacetate of Example F using the chloride of Example H derived from the less polar pair of racemates (0.62 g, 0.002 mole) and potassium thioacetate (917 mg) in DMF (15 ml). The crude product was chromatographed on silica gel using 10% ethyl acetate/hexane to give 0.57 g of the titled product (Product A.)

In a similar manner, chloride of Example H derived from the more polar pair of racemates (1.3 g, 0.0042 mol) was converted to desired thioacetate (0.09 g, Product B).

Example J

Preparation of ethyl 2-(mercaptomethyl)-1,4-dithiaspiro[4.5]decane-7-acetate

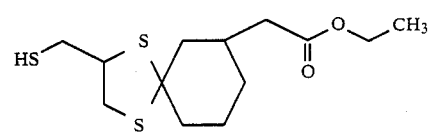

The titled compound was prepared according to the procedure described in Example G using 0.55 g (0.0016 mol) of product A of Example I derived from the less polar pair of racemates of Example H. This product was treated with sodium ethoxide (prepared from 40 mg Na metal in 5 ml of ethanol) at room temperature of 1 hr under $N_2$. After chromatography of the crude product on silica gel, 400 mg of the titled product was obtained.

In a similar manner product B (0.90 g) of Example I (derived from the more polar pair of racemates of Example H) was converted to the titled product (0.70 g).

Example K

Preparation of ethyl 2-(hydroxymethyl)-1,4-dioxaspiro[4.4]nonane-7-acetate

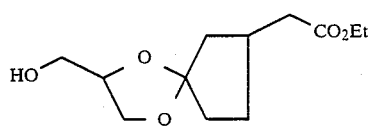

The ketoester (17.02 g, 0.1 mole), glycerol (9.21 g, 0.1 mol) and p-toluenesulfonic acid (100 mg) are combined in benzene (150 ml) and refluxed with stirring for 10 hr using a water separator to remove water formed during the ketalization. The reaction mixture is cooled, washed with 5% NaOH solution and water and then dried over sodium sulfate. The drying agent is filtered and the filtrate stripped on a rotary evaporator to give the titled product. The product is purified by chromatography on silica gel using mixtures of ethyl acetate and hexane as eluents.

Example L

Preparation of ethyl 2-[[[(4-methylphenyl)sulfonyl]oxy]methyl]-1,4-dioxaspiro[4.4]nonane-7-acetate

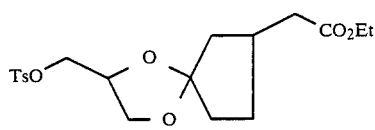

To a cold (0°) stirred solution of the alcohol of Example K (2.44 g, 10 mmol) in pyridine (30 ml) is added p-toluenesulfonyl chloride (1.91 g, 10 mmol) in portions over 15 minutes. When addition is completed, the reaction mixture is stirred at room temperature for 2 hrs. The reaction mixture is diluted with ether and washed successively with water, 0.5N aqueous sodium bisulfate solution, 5% aqueous sodium bicarbonate solution and water. The organic layer is dried over sodium sulfate, filtered, and the filtrate is concentrated on the rotary evaporator to give the titled compound.

Example M

Preparation of ethyl 2-[(acetylthio)methyl]-1,4-dioxaspiro[4.4]nonane-7-acetate

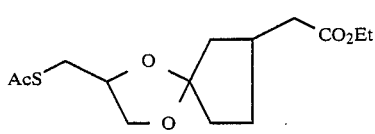

A stirred slurry of potassium thioacetate (1.14 g, 10 mmol) in a solution of the tosylate of Example L (4.14 g, 10 mmol) in acetone (30 ml) is refluxed under nitrogen for 5 hrs. The reaction mixture is filtered and the filtrate is concentrated on a rotary evaporator. The residue is dissolved in ethyl acetate, washed with water and dried over sodium sulfate. The drying agent is filtered, the solvent is removed using the rotary evaporator and the residue is chromatrographed on silica gel using mixtures of ethyl acetate and hexane as eluents to give the titled compound.

Example N

Preparation of ethyl 2-(mercaptomethyl)-1,4-dioxaspiro[4.4]nonane-7-acetate

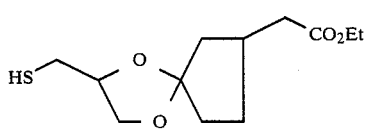

Sodium ethoxide is prepared in ethanol (27 ml) using sodium metal (230 mg). Thioacetate of Example M (3.02 g, 10 mmol) is added and the reaction mixture is stirred at room temperature under a nitrogen atmosphere for 2 hours. The reaction mixture is poured into 0.5N KHSO4, extracted with ethyl acetate and dried over Na2SO4. The drying agent is filtered, the filtrate concentrated in vacuo and the residue chromatographed on silica gel using mixtures of ethyl acetate and hexane as eluents to give the titled compound.

Example O

Preparation of ethyl 2-(hydroxymethyl)-1-oxa-4-thiaspiro[4.4]nonane-7-acetate

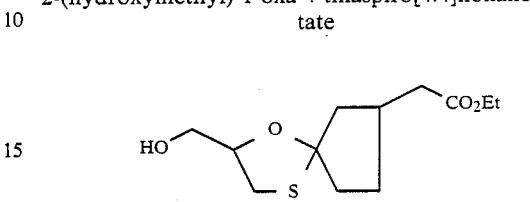

17.02 g (0.1 mol) of the appropriate ketoester and 10.8 g (0.1 mol) of 3-mercapto-1,2-propanediol are dissolved in methylene chloride (600 ml). Distilled baron trifluoride etherate (2.5 ml) is added and the reaction is stirred for three days at room temperature under a nitrogen atmosphere.

The reaction is quenched by adding 5% aqueous potassium bicarbonate solution (200 ml). The layers are separated and the organic phase is washed with water and dried over magnesium sulfate. The drying agent is filtered and the filtrate is concentrated on a rotary evaporator. The residual oil is chromatographed on silica gel using mixtures of ethyl acetate and toluene as eluents to give the above titled compound.

Example P

Preparation of ethyl 2-[[[(4-methylphenyl)sulfonyl]oxy]methyl]-1-oxa-4-thiaspiro[4.4]nonane-7-acetate

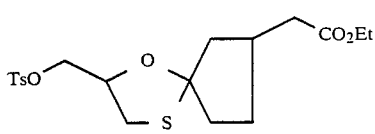

To a cold stirred solution of the product of Example O (2.60 g, 10 mmol) in pyridine (30 ml) is added p-toluenesulfonyl chloride (1.91 g, 10 mmol) in portions over 15 minutes. When the addition is completed the reaction is stirred at room temperature for 2 hrs. The reaction mixture is diluted with ether and washed with water, 0.5N aqueous sodium bisulfate solution, 5% aqueous sodium bicarbonate solution and water. The organic layer is dried over sodium sulfate, filtered, and the filtrate is concentrated on a rotary evaporator to give the titled compound.

Example Q

Preparation of ethyl 2-[(acetylthio)methyl]-1-oxa-4-thiaspiro[4.4]nonane-7-acetate

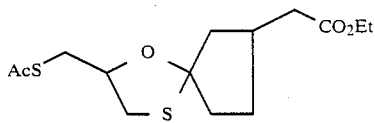

A stirred slurry of potassium thioacetate (1.14 g, 10 mmol) in a solution of the tosylate of Example P (4.15 g, 10 mmol) in acetone (30 ml) is refluxed under nitrogen for 5 hrs. The reaction mixture is filtered and the filtrate is concentrated on a rotary evaporator. The residue is dissolved in ethyl acetate, washed with water and dried over sodium sulfate. The drying agent is filtered, the solvent is removed using the rotary evaporator and the residue is chromatographed on silica gel using mixtures of ethyl acetate and hexane as eluents to give the titled compound.

Example R

Preparation of ethyl 2-(metcaptomethyl)-1-oxa-4-thiaspiro[4.4]nonane-7-acetate

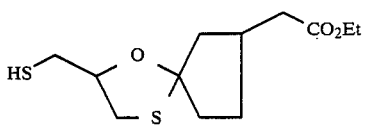

A solution of sodium ethoxide (prepared from 230 mg. of sodium metal) in ethanol (20 ml) and the thioacetate of Example Q (3.18 g, 10 mmol) is stirred for one hour at room temperature under nitrogen. Ethanol is removed in vacuo on the rotary evaporator and the residue is dissolved in ethyl acetate. This organic phase is washed with 0.5N sodium bisulfate solution and dried over sodium sulfate. The drying agent is filtered and the filtrate concentrated on a rotary evaporator to give the titled compound.

DESCRIPTION OF THE PREFERRED EMBODIMENTS

Example 1

Preparation of ethyl 3-[[[3-(4-acetyl-3-hydroxy-2-propylphenoxy)propyl]thio]methyl]-1-oxa-4-thiaspiro[4.4]nonane-7-acetate

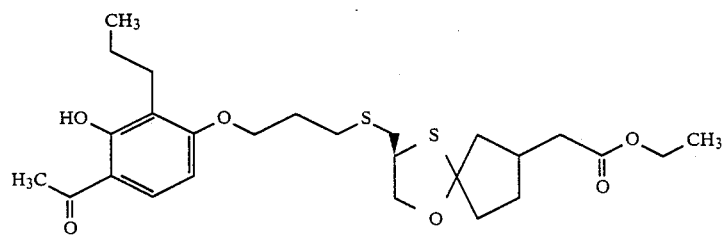

A solution of the titled compound of Example A (2.0 g), 7.0 mmol) and 3-(2-n-propyl-3-hydroxy-4-acetylphenoxy)-1-bromopropane (2.3 g), 7.2 mmol), prepared by the method described in U.S. Pat. No. 4,565,882, Example 14, incorporated herein by reference, in methyl ethyl ketone containing suspended potassium carbonate (2.5 g) was refluxed with stirring under $N_2$ for 15 hrs. The reaction was cooled and filtered and the filtrate concentrated on a rotary evaporator. The residue was chromatographed on silica gel using 20% ethyl acetate/hexane as the eluent to give 3.5 g (95%) of the titled compound.

Anal. Calcd. for $C_{26}H_{38}O_6S_2$: C, 61.16; H, 7.50; S, 12.53. Found: C, 61.09; H, 7.43; S, 12.42.

Example 2

Preparation of 3-[[[3-(4-acetyl-3-hydroxy-2-propylphenoxy)propyl]thio]methyl]-1-oxa-4-thiaspiro[4.4]nonane-7-acetic acid

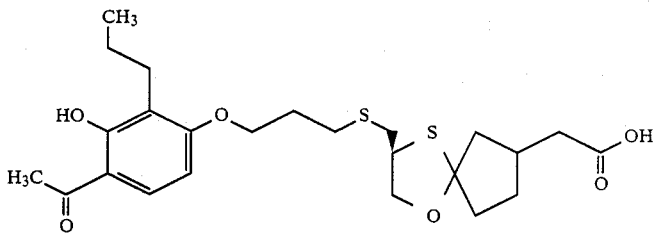

A solution of the titled compound of Example 1 ethyl 3-[[[3-(4-acetyl-3-hydroxy-2-propylphenoxy)-propyl]-thio]methyl]-1-oxa-4-thiaspiro[4.4]nonane-7-acetate (3.0 g, 5.9 mmol) and 2M lithium hydroxide solution (7.5 ml), 2.5 e.q.) in ethanol (35 ml) was stirred overnight at room temperature under $N_2$. The solvent was removed in vacuo and the residue diluted with water. After acidification to pH 2.5 with 0.5N $KHSO_4$, the mixture was extracted with ethyl acetate and dried over magnesium sulfate. The drying agent was filtered and the filtrate concentrated in vacuo to give an oil. Further drying of the oil at 60° (0.5 torr) for 4 hr gave 2.58 g (91%) of the titled compound as an oil.

Anal. Calcd. for $C_{24}H_{34}S_2O_6$: C, 59.73; H, 7.10: S, , 13.26. Found: C, 59.70; H, 7.30; S, 13.02.

Resolution of the titled compound may be accomplished by conventional methods.

Example 3

Preparation of ethyl 3-[[[3-(4-acetyl-3-hydroxy-2-propylphenoxy)propyl]thio]methyl]-1-oxa-4-thiaspiro[4.5]decane-7-acetate

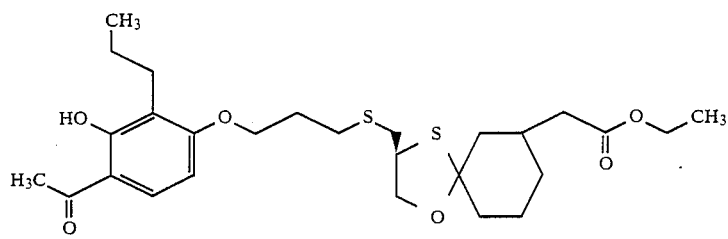

The titled compound is prepared using the product of Example C and the procedure of Example 1. Chromatography of the crude product on silica gel using mixtures of ethyl acetate/hexane as eluents gives the titled compound.

Example 4

Preparation of 3-[[[3-(4-acetyl-3-hydroxy-2-propylphenoxy)propyl]thio]methyl]-1-oxa-4-thiaspiro[4.5]decane-7-acetate

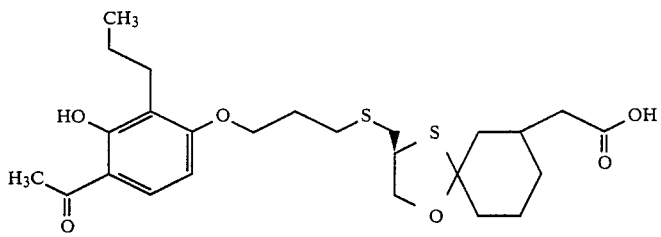

Using aqueous 2M LiOH (9 ml) in EtOH 3.2 g (0.0061 mmol) of the product of Example 3 and following the procedure described in Example 2, the titled compound is obtained as an oil.

Example 5

Preparation of ethyl 3-[[[2-(4-acetyl-3-hydroxy-2-propylphenoxy)propyl]thio]methyl]-1,4-dithiaspiro[4.4-]nonane-7-acetate

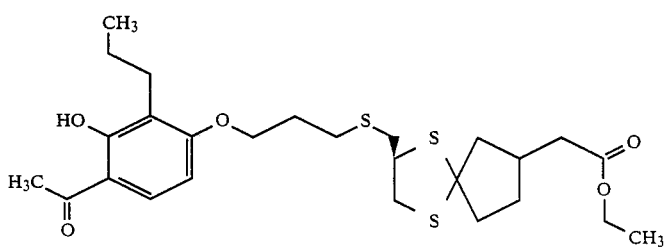

A mixture of $K_2CO_3$ (2.5 g) and a solution of product of Example G (2.1 g, 7.2 mmol) and bromide (2.25 g, 7.2 mmol) in methyl ethyl ketone was refluxed under $N_2$ with stirring for 24 hrs. The reaction was filtered, concentrated on a rotary evaporator and the residue chromatographed on silica gel using 30% ethyl acetate/hexane to give 3.5 g (92%) of the titled compound as an oil.

Anal. Calcd. for $C_{26}H_{38}O_5S_3$: C, 59.30; H, 7.27; S, 18.03. Found: C, 59.07; H, 7.50; S, 17.60.

Example 6

Preparation of 3-[[[2-(4-acetyl-3-hydroxy-2-propylphenoxy)propyl]thio]methyl]-1,4-dithiaspiro[4.4]nonane-7-acetic acid

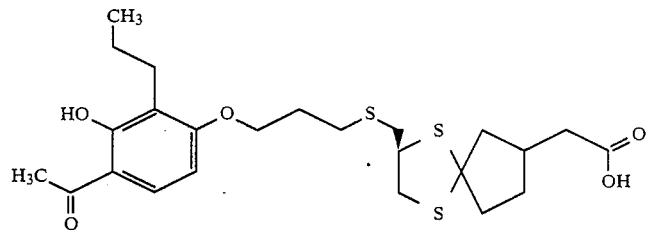

The product of Example, 5 (3.3 g, 0.0061 mol) was converted to the titled compound using aqueous 2M LiOH (8 ml, 2.5 eq) in ethanol (40 ml) according to the procedure used for the synthesis described in Example 2. After drying the product at 60° (0.5 torr), there was obtained 3.0 g (97% yield) of the titled compound.

Anal. Calcd. for $C_{24}H_{34}O_5S_3$: C, 57.82; H, 6.87; S, 19.28. Found: C, 57.50; H, 6.88; S, 19.51.

Example 7

Preparation of ethyl 2-[[[3-(4-acetyl-3-hydroxy-2-propylphenoxy)propyl]thio]methyl]-1,4-dithiaspiro[4.5]decane-7-acetate

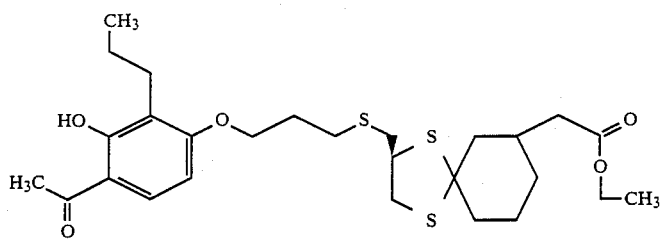

A mixture of K₂CO₃ (450 mg) a solution of the product of Example J (derived from product A of Example I) (400 mg, 0.0013 mol) and the bromide compound (411 mg, 0.0013 mol) in methyl ethyl ketone (10 ml) was refluxed with stirring under N₂ for 24 hrs. The reaction was worked up following the procedure described in Example 5. The crude product was purified by chromatography on silica gel using mixtures of ethyl acetate and hexane as eluents to give 650 mg of titled compound (mixture of racemates).

The product of Example J (derived from product B of Example I) (0.70 g) was converted to the titled compound (1.23 g) in 94% yield (mixture of racemates).

Example 8

Preparation of 2-[[[3-(4-acetyl-3-hydroxy-2-propylphenoxy)propyl]thio]methyl]-5β-1,4-dithiaspiro[4,5]decan-7-acetic acid

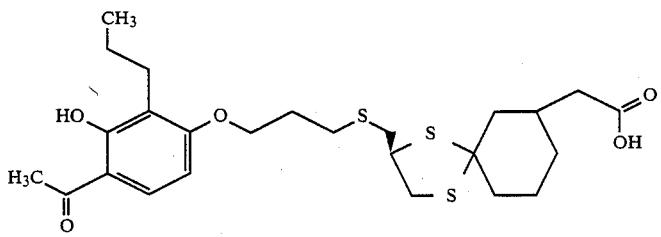

Using aqueous 2M LiOH (2 ml) in EtOH (15 ml) 625 mg (0.0011 mol) of the racemates of Example 7 (ultimately derived from product A of Example I) was converted to the titled product using the same procedure described in Example 1. After drying at 65° C. (0.5 torr) for 4 hrs. there was obtained 532 mg of the titled product (ultimately derived from product A of Example I.

Anal. Calcd. for $C_{25}H_{36}O_5S_3$: C, 58.58; H, 7.08; S, 18.73. Found: C, 58.36; H, 7.12; S, 18.63.

Using aqueous 2M LiOH (4 ml) in EtOH (30 ml) 1.2 g (0.0022 mol) of the racemates of Example 7 (ultimately derived from product B of Example I) was converted to the titled product using the same procedure described in Example 1. After drying at 65° C. (0.5 torr) for 4 hrs. there was obtained 936 mg of the titled product (ultimately derived from product B of Example I).

Anal. Calcd. for $C_{25}H_{36}O_5S_3$: C, 58.58; H, 7.08; S, 18.73. Found: C, 58.54; H, 7.17; S, 18.71.

Example 9

Preparation of 3-[[[3-(4-acetyl-3-hydroxy-2-propylphenoxy)propyl]sulfinyl]methyl]-1-oxa-4-thiaspiro[4.4]nonane-7-acetic acid

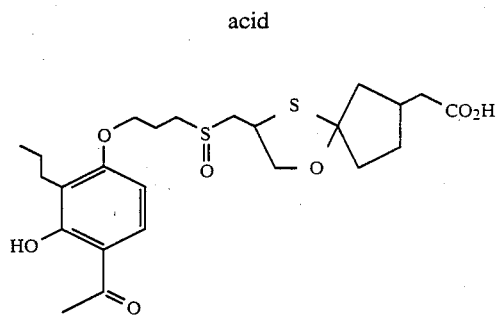

To a cold (0° C.), stirred solution of the sulfide from Example 2 (250 mg, 0.52 mmol) in methylene chloride (2 ml) is added 85% m-chloroperbenzoic acid (106 mg, 0.52 mmol). After stirring 2 hrs. at 0° C., the solvent is evaporated using a nitrogen stream and the residue is chromatographed on silica gel using ethyl acetate containing 0.5% acetic acid as eluent to give the titled compound.

Example 10

Preparation of ethyl 3-[[[3-(4-acetyl-3-hydroxy-2-propylphenoxy)-2-hydroxypropyl]thio]methyl]-1-oxa-4-thiaspiro[4.4]nonane-7-acetate

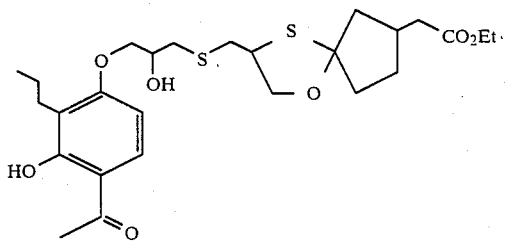

3-(2-n-Propyl-3-hydroxy-4-acetylphenoxy)-1,2-epoxypropane (1.5 g, 0.006 mol) (described in U.S. Pat. No. 4,565,882) is dissolved in 20 ml of methyl ethyl ketone. To this solution is added the mercaptan of Example G (1.75 g, 0.006 mol) and anhydrous potassium carbonate (2.5 g) and the reaction mixture is refluxed with stirring under a nitrogen atmosphere for 24 hrs. The reaction is cooled to room temperature, filtered and the filtrate is concentrated on a rotary evaporator. The residue is chromatographed on silica gel using mixtures of ethyl acetate and hexane as eluents to give the titled compound.

Example 11

Preparation of ethyl 3-[[[3-4-acetyl-3-methoxy-2-propylphenoxy)propyl]thio]methyl]-1-oxa-4-thiaspiro[4.4]nonane-7-acetate

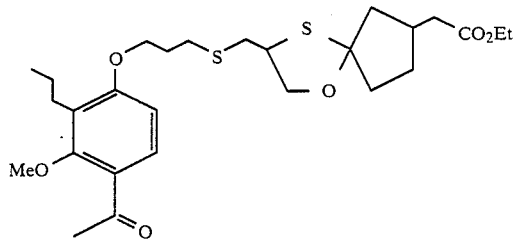

3-(2-n-Propyl-3-methoxy-4-acetylphenoxy)-1-bromopropane (1.24 g, 0.037 mol) is dissolved in 15 ml of methyl ethyl ketone containing the mercaptan of Example G (1.08 g, 0.0037 mol). To this solution is added anhydrous potassium carbonate (1.0 g, 7.24 mmol) and the mixture is refluxed for 14 hrs. under an argon atmosphere. The reaction is cooled and filtered and the filtrate is evaporated. The residue is chromatographed on silica gel using mixtures of ethyl acetate and toluene as eluents to give the titled compound.

Example 12

Preparation of 3-[[[3-(4-acetyl-3-methoxy-2-propylphenoxy)propyl]thio]methyl]-1-oxa-4-thiaspiro[4.4]nonane-7-acetic acid

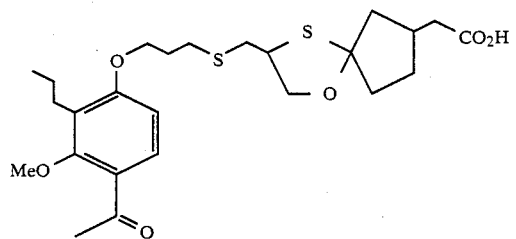

The product of the above example is saponified according to the procedure described in Example 2 using 0.75 g (0.0016 mol) of the ester of Example 11 and 2M LiOH solution (2.0 ml, 2.5 eq) in ethanol (10 ml). After stirring overnight at room temperature, the solvent is removed in vacuo and the residue diluted with water. After acidification to pH 2.5 with 0.5N KHSO$_4$, the mixture is extracted with ethyl acetate and dried over magnesium sulfate. The drying agent is filtered and the filtrate is concentrated in vacuo. Further drying at 60° (0.5 torr) gives the titled compound.

Example 13

Preparation of ethyl 2-[[[3-(4-acetyl-3-hydroxy-2-propylphenoxy)propyl]thio]methyl]-1,4-dioxaspiro[4.4]nonane-7-acetate

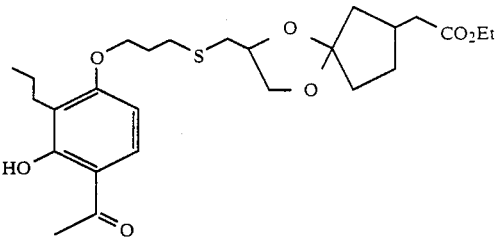

A mixture of K$_2$CO$_3$ (3.45 g) and a solution of the titled compound of Example N (2.60 g, 10 mmol) and 3-(2-n propyl-3-hydroxy-4-acetylphenoxy)-1-bromopropane (3.15 g, 10 mmol) in methyl ethyl ketone (50 ml) is refluxed with stirring under N$_2$ for 12 hours.

The reaction is cooled and filtered. The filtrate is concentrated in vacuo and the oily residue chromatographed on silica gel using mixtures of ethyl acetate and hexane as eluents to give the titled compound.

Example 14

Preparation of 2-[[[3-(4-acetyl-3-hydroxy-2-propylphenoxy)propyl]thio]methyl]-1,4-dioxaspiro[4.4]nonane-7-acetic acid

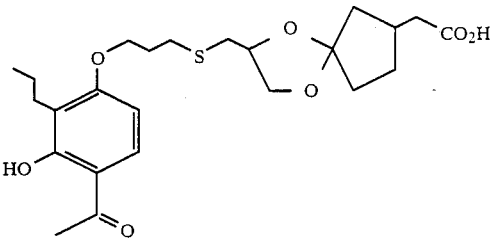

The ester of Example 13 (4.87 g, 10 mmol) is stirred overnight at room temperature under N$_2$ with aqueous LiOH solution (2M, 13 ml) in methanol (60 ml). The reaction is concentrated on a rotary evaporator and the residue diluted with water. The resulting solution is washed once with ethyl ether and then acidified to pH 2.5 with 0.5N KHSO$_4$ solution. The aqueous mixture is extracted with ethyl acetate and the organic layer dried over MgSO$_4$.

The drying agent is filtered and the filtrate is concentrated on a rotary evaporator to give an oily residue which is purified by chromatography on silica gel using mixtures of ethyl acetate and hexane containing 0.5% acetic acid as eluents. The purified product is evaporated with methanol and benzene to remove acetic acid. The resulting product is dried on the oil pump (0.1 mm Hg) at 60° to give the titled compound.

Example 15

Preparation of ethyl 2-[[[3-(4-acetyl-3-hydroxy-2-propylphenoxy)propyl]thio]methyl]-1-oxa-4-thiaspiro[4.4]nonane-7acetate

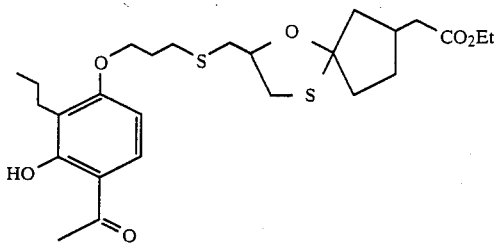

A mixture of K$_2$CO$_3$ (3.45 g) and a solution of the mercaptan (2.76 g, 10 mmol) of Example R and 3-(2-n propyl-3-hydroxy-4-acetyl phenoxy)-1-bromo propane (3.15 g, 10 mmol) in methyl ethyl ketone (50 ml) is refluxed with stirring under N$_2$ for 12 hrs. The reaction is cooled and filtered. The filtrate is concentrated in vacuo and the oily residue chromatographed on silica gel using mixtures of ethyl acetate and hexane as eluents to give the titled product.

Example 16

Preparation of 2-[[[3-(4-acetyl-3-hydroxy-2-propylphenoxy)propyl]thio]methyl]-1-oxa-4-thiaspiro[4.4]nonane-7-acetic acid

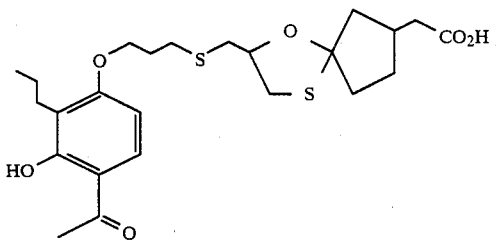

The ester of Example 15 (4.87 g, 10 mmol) is stirred overnight at room temperature under N$_2$ with aqueous LiOH solution (2M, 13 ml) in methanol (60 ml). The reaction is concentrated on a rotary evaporator and the residue diluted with water. The resulting solution is washed once with ethyl ether and then acidified to pH 2.5 with 0.5N KHSO$_4$ solution. The aqueous mixture is extracted with ethyl acetate and the organic layer dried over MgSO$_4$.

The drying agent is filtered and the filtrate is concentrated on a rotary evaporator to give an oily residue which is purified by chromatography on silica gel using mixtures of ethyl acetate and hexane containing 0.5% acetic acid as eluents. The purified product is evaporated with methanol and benzene to remove acetic acid. The resulting product is dried on the oil pump (0.1 mm Hg) at 60° to give the titled compound.

Example 17

Preparation of 3-[[[3-(4-acetyl-3-hydroxy-2-propylphenoxy)-2-hydroxypropyl]thio]methyl]-1-oxa-4-thiaspiro[4.4]nonane-7-acetic acid

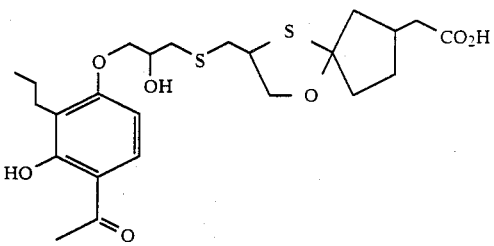

The product of Example 10 is saponified according to the procedure of Example 2 using 5.3 g (10 mmol) of the above ester and 2M LiOH solution (12.5 ml, 2.5 eq.) in ethanol (50 ml). After stirring overnight at room temperature, the solvent is removed in vacuo and the residue diluted with water. After acidification to pH 2.5 with 0.5N KHSO$_4$, the mixture is extracted with ethyl acetate and dried over magnesium sulfate. The drying agent is filtered and the filtrate is concentrated in vacuo. Further drying of the resultant residue at 60° (0.5 torr) gives the titled compound.

What is claimed is:

1. A compound of the formula

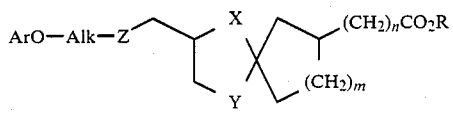

or the pharmaceutically acceptable salts or geometrical or optical isomers thereof wherein: Alk is alkylene or hydroxyalkylene containing 1–6 carbon atoms;
  Ar is 5,6,7,8-tetrahydro-1-naphthalenyl or phenyl unsubstituted or substituted with one or more substituents selected from lower alkyl containing 1 to 6 carbon atoms, and lower alkanoyl containing 1 to 6 carbon atoms;
  R is hydrogen or alkyl containing 1 to 6 carbon atoms
  X, Y, and Z are each independently O or S wherein 5 may be oxidized to S=O;
  m is an integer from 0 to 3;
  n is an integer from 0 to 5.

2. A compound according to claim 1, wherein Alk is alkylene containing 1–6 carbon atoms; Ar is phenyl substituted with lower alkyl containing 1 to 6 carbon atoms, hydroxy and lower alkanoyl containing 1 to 6 carbon atoms; R is hydrogen or lower alkyl containing 1 to 6 carbon atoms; m is the integer 1 or 2; and n is the integer 1 or 2.

3. A compound according to claim 2, of the formula

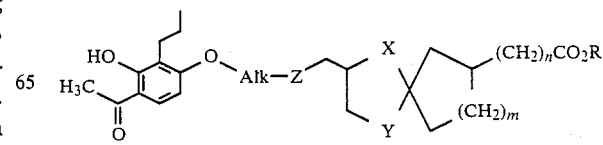

and the pharmaceutically acceptable salts and geometrical and optical isomers thereof.

4. A compound according to claim 3, which is ethyl 2-[[[3-(4-acetyl-3-hydroxy-2-propylphenoxy)propyl]thio]methyl]-1,4-dithiaspiro[4.4]nonane-7-acetate and isomers thereof.

5. A compound according to claim 3 which is 2-[[[3-(4-acetyl-3-hydroxy-2-propylphenoxy)propyl]thio]methyl]-1,4-dithiaspiro[4.4]nonane-7-acetic acid and isomers thereof.

6. A compound according to claim 3, which is 3-[[[.3-(4-acetyl-3-hydroxy-2-propylphenoxy)propyl]thio]methyl]-1-oxa-4-thiaspiro[4.4]nonane-7-acetic acid and isomers thereof.

7. A compound according to claim 3, which is ethyl 3-[[[3-hydroxy-2-propylphenoxy)propyl]-thio]methyl]-1-oxa-4-thiaspiro[4.4]nonane-7acetate and isomers thereof.

8. A compound according to claim 3 which is 2-[[[3-(4-acetyl-3-hydroxy-2-propylphenoxy)propyl]-thio]methyl]-1,4-dithiaspiro[4,5]decane-7-acetic acid and isomers thereof.

9. A pharmaceutical composition comprising at least one compound according to claim 1, together with one or more non-toxic pharmaceutically acceptable carriers.

10. A pharmaceutical composition according to claim 9 wherein said compound is selected from the group consisting of:

Ethyl 2-[[[3-(4-acetyl-3-hydroxy-2-propylphenoxy)propyl]thio]methyl]-1,4-dithiaspiro[4.4]nonane-7-acetate and isomers thereof;

2-[[[3-(4-Acetyl-3-hydroxy-2-propylphenoxy)propyl]thio]methyl]-1,4-dithiaspiro[4.4]nonane-7-acetic acid and isomers thereof;

Ethyl 3-[[[3-(4-acetyl-3-hydroxy-2-propylphenoxy)propyl]thio]methyl]-1-oxa-4-thiaspiro[4.4]nonane-7-acetate and isomers thereof;

3-[[[3-(4-Acetyl-3-hydroxy-2-propylphenoxy)propyl]thio]methyl]-1-oxa-4-thiaspiro[4.4]-.nonane07-acetic acid and isomers thereof; and 2-[[[3-(4-Acetyl-3-hydroxy-2-propylphenoxy)propyl]thio]methyl]-1,4-dithiaspiro[4,5]decane-7-acetic acid and isomers thereof.

11. A method of treating allergy comprising administering a therapeutically effective dose of at least one compound of claim 1 to a mammal in need of such treatment.

12. A method according to claim 11, wherein said compound is selected from the group consisting of:

Ethyl 2-[[[3-(4-acetyl-3-hydroxy-2-propylphenoxy)propyl]thio]methyl]-1,4-dithiaspiro[4.4]nonane-7-acetate and isomers thereof;

2-[[[3-(4-Acetyl-3-hydroxy-2-propylphenoxy)propyl]thio]methyl]-1,4-dithiaspiro[4.4]nonane-7-acetic acid and isomers thereof;

Ethyl 3-[[[3-(4-acetyl-3-hydroxy-2-propylphenoxy)propyl]thio]methyl]-1-oxa-4-thiaspiro[4.4]nonane-7-acetate and isomers thereof;

3-[[[3-(4-Acetyl-3-hydroxy-2-propylphenoxy)propyl]thio]methyl]-1-oxa-4-thiaspiro[4.4]nonane-7-acetic acid and isomers thereof; and 2-[[[3-(4-Acetyl-3-hydroxy-2-propylphenoxy)propyl]thio]methyl]-1,4-dithiaspiro[4.5]decane-7-acetic acid and isomers thereof.

13. A method of treating inflammatory diseases comprising administering a therapeutically effective amount of a compound of claim 1 to an animal in need of such treatment.

* * * * *

UNITED STATES PATENT AND TRADEMARK OFFICE
CERTIFICATE OF CORRECTION

PATENT NO. : 4,870,098
DATED : September 26, 1989
INVENTOR(S) : Stealey, et al.

It is certified that error appears in the above-identified patent and that said Letters Patent is hereby corrected as shown below:

Column 3, the last structure, that portion of the structure reading  should read 

Column 5, the first structure, that portion of the structure reading  should read 

Column 6, the first structure, that protion of the structure reading  should read 

Column 9, line 24, reading "X and S" should read -- X is S --.

Column 9, line 29, reading "(1949)" should read -- 1940 --.

Column 10, line 67, reading "Formula 10" should read -- Formula 20 --.

Columns 10 and 11, lines 68 and 1, respectively, reading "-4acetyl-phenoxy-1-" should read -- 4-acetylphenoxy)-1- --.

Column 15, line 22, reading "4thiaspiro" should read --4-thiaspiro --.

Column 23, line 21, reading "acetate" should read -- acetic acid --.

Column 27, line 16, reading "-4-acetyl" should read -- -(4-acetyl --.

Column 29, line 6, reading "7acetate" should read -- 7-acetate --.

Column 30, line 45, reading "6 carbon atoms," should read -- 6 carbon atoms, hydroxy, lower alkoxy containing 1 to 6 carbon atoms, --.

UNITED STATES PATENT AND TRADEMARK OFFICE
CERTIFICATE OF CORRECTION

PATENT NO. : 4,870,098
DATED : September 26, 1989
INVENTOR(S) : Stealey, et al.

It is certified that error appears in the above-identified patent and that said Letters Patent is hereby corrected as shown below:

Column 30, line 49, read "5" should read -- S --.

Column 31, line 12, Claim 6, reading "[[[.3" should read -- [[[3 --.

Column 31, lines 16-18, Claim 7, reading "ethyl 3-[[[3-hydroxy-2-propylphenoxy)propyl]-thio]methyl]-1-oxa-4-thiaspiro[4.4]nonane-7acetate" should read -- ethyl 3-[[[3-(4-acetyl-3-hydroxy-2-propylphenoxy)propyl]-thio]methyl]-1-oxa-4-thiaspiro[4.4]nonane-7-acetate.

Column 32, line 6, reading ".nonane07-acetic" should read -- nonane-7-acetic --.

Signed and Sealed this

Second Day of April, 1991

Attest:

HARRY F. MANBECK. JR.

Attesting Officer

Commissioner of Patents and Trademarks